United States Patent
Reif et al.

(10) Patent No.: US 6,540,882 B1
(45) Date of Patent: Apr. 1, 2003

(54) PROCESSES FOR THE SYNTHESIS OF PENTAFLUOROBUTANE AND THE SEPARATION OF HYDROGEN FLUORIDE AND PENTAFLUOROBUTANE MIXTURES

(75) Inventors: Ferdinand Reif, Brussels (BE); Dominique Balthasart, Brussels (BE)

(73) Assignee: Solvay (Societe Anonyme) (BE)

( * ) Notice: Subject to any disclaimer, the term of this patent is extended or adjusted under 35 U.S.C. 154(b) by 0 days.

(21) Appl. No.: 09/533,425

(22) Filed: Mar. 22, 2000

(30) Foreign Application Priority Data

Mar. 24, 1999 (FR) .............................. 99 03918

(51) Int. Cl.⁷ .................. B01D 3/36; C07C 17/383; C01B 7/19
(52) U.S. Cl. ................. 203/77; 203/80; 570/177; 570/178; 423/483
(58) Field of Search .............. 203/43, 80, 67, 203/73, 36–37, 77, 74; 570/177, 178, 167, 164; 423/483

(56) References Cited

U.S. PATENT DOCUMENTS

| | | | | |
|---|---|---|---|---|
| 4,911,792 A | * | 3/1990 | Manzer et al. ................ 203/39 |
| 4,950,364 A | * | 8/1990 | Wismer ....................... 203/98 |
| 5,346,595 A | * | 9/1994 | Clemmer et al. ............ 570/178 |
| 5,626,725 A | * | 5/1997 | Balthasart et al. ............. 203/80 |
| 5,739,406 A | * | 4/1998 | Pennetreau et al. ......... 570/167 |
| 5,847,244 A | * | 12/1998 | Shibanuma et al. ........ 570/169 |
| 5,918,481 A | * | 7/1999 | Pham et al. .................. 62/631 |
| 5,948,381 A | | 9/1999 | Eibeck et al. |
| 6,294,055 B2 | * | 9/2001 | Herkelmann et al. ......... 203/43 |

FOREIGN PATENT DOCUMENTS

| | | |
|---|---|---|
| EP | 699649 | 3/1996 |
| EP | 885863 | 12/1998 |
| WO | 97/13719 | 4/1997 |

* cited by examiner

Primary Examiner—Virginia Manoharan
(74) Attorney, Agent, or Firm—Connolly Bove Lodge & Hutz LLP

(57) ABSTRACT

The invention relates to a process of separation of mixtures containing HFC-365mfc/HF azeotropic compositions by two distillations at different pressures, as well as to a process of synthesis of HFC-365mfc which integrates this process of separation and a recycling of certain fractions towards the hydrofluorination step.

18 Claims, 1 Drawing Sheet

PROCESSES FOR THE SYNTHESIS OF PENTAFLUOROBUTANE AND THE SEPARATION OF HYDROGEN FLUORIDE AND PENTAFLUOROBUTANE MIXTURES

FIELD OF INVENTION

The present invention relates to a process for the separation of mixtures comprising optionally azeotropic or pseudoazeotropic compositions. which contain hydrogen fluoride and 1,1,1,3,3-pentafluorobutane; and to a process for the synthesis of 1,1,1,3,3-pentafluorobutane.

BACKGROUND OF THE INVENTION 1,1,1,3,3-Pentafluorobutane (HFC-365mfc) may be prepared by reaction of a suitable chloro precursor with hydrogen fluoride, as described for example in patent application EP-A1-0699649 in the name of SOLVAY. In such a process, on leaving the hydrofluorination reactor, the reaction product mixture contains, besides the desired 1,1,1,3,3-pentafluorobutane, hydrogen chloride originating from the elimination of the chlorine atom(s) in the starting chloro precursor, hydrogen fluoride and optionally inert diluents, as well as small amounts of various intermediates or by-products. Given that the process is usually performed with an excess of hydrogen fluoride relative to the chloro precursor, unconverted hydrogen fluoride usually remains in the reaction product mixture.

SUMMARY OF THE INVENTION

It is, desirable to have processes which make it possible to separate the 1,1,1,3,3-pentafluorobutane efficiently from the reaction product mixture. At the same time, it is desirable to ensure good use of raw materials, in particular of the hydrogen fluoride.

Consequently, the invention relates to a process for the separation of at least one constituent from a mixture comprising 1,1,1,3,3-pentafluorobutane and hydrogen fluoride, according to which the mixture is subjected to at least two distillations, the first distillation being carried out at a first pressure and the second distillation being carried out at a second pressure which is different from the first, and at least one fraction enriched in 1,1,1,3,3-pentafluorobutane and at least one fraction enriched in hydrogen fluoride are recovered.

It has been found, surprisingly, that the process according to the invention makes it possible to isolate 1,1,1,3,3-pentafluorobutane and hydrogen fluoride which are essentially pure, in particular from mixtures comprising 1,1,1,3,3-pentafluorobutane and hydrogen fluoride in proportions at which they form an azeotrope or a pseudoazeotrope.

The process according to the invention also makes it possible to isolate azeotropic fractions at a given pressure which are enriched either in hydrogen fluoride or in 1,1,1,3,3-pentafluorobutane.

In a variant of the process according to the invention, the first distillation is carried out at a higher pressure and the second distillation is carried out at a lower pressure.

In another variant of the process according to the invention, the first distillation is carried out at a lower pressure and the second distillation is carried out at a higher pressure.

The lower pressure to be used in the process according to the invention is generally at least 0.5 bar. Often this pressure is at least 0.9 bar. Generally the lower pressure is at most 3 bar. Often this pressure is at most 2.5 bar. Preferably the lower pressure is 1 to 2 bar.

The temperature at which the distillation at lower pressure is carried out is generally at least 0° C. The temperature is often at least 10° C. The temperature is generally at most 60° C. Often, the temperature is at most 40° C. Preferably, the temperature at which the distillation at lower pressure is carried out is 15 to 30° C.

The higher pressure to be used in the process according to the invention is generally at least 6 bar. Often this pressure is at least 7 bar. Generally the higher pressure is at most 12 bar. Often this pressure is at most 11 bar. Preferably the higher pressure is 8 to 10 bar.

The temperature at which the distillation at higher pressure is carried out is generally at least 70° C. The temperature is often at least 80° C. The temperature is generally at most 150° C. Often, the temperature is at most 120° C. Preferably, the temperature at which the distillation at higher pressure is carried out is 80 to 100° C.

The 1,1,1,3,3-pentafluorobutane content in the fraction enriched in 1,1,1,3,3-pentafluorobutane is often at least 50 mol %. More often it is at least 75 mol %. In a preferred variant, an enriched fraction consisting essentially of 1,1,1,3,3-pentafluorobutane is recovered, for example with a 1,1,1,3,3-pentafluorobutane content of at least 99 mol %.

The hydrogen fluoride content in the fraction enriched in hydrogen fluoride may be at least 99 mol %. It may be at least 99.5 mol %. In a variant, an enriched fraction consisting essentially of hydrogen fluoride is recovered.

Techniques and equipment which can be used to carry out the distillations in the process according to the invention are well known.

The mixture to which the process of separation according to the invention is applied may be, for example, a reaction mixture which is derived from a process of synthesis of 1,1,1,3,3-pentafluorobutane by hydrofluorination of a chloro precursor such as for example the process mentioned above. The process is often applied to mixtures comprising hydrogen fluoride and 1,1,1,3,3-pentafluorobutane in proportions at which they form an azeotrope or a pseudoazeotrope.

In a variant of the process according to the invention, the mixture used is a mixture which contains an azeotropic composition consisting essentially of 1,1,1,3,3-pentafluorobutane and hydrogen fluoride and optionally comprising, in addition, hydrogen chloride, chloro(fluoro)butanes of general formula (I)

$$CCl_aF_{3-a}CH_2CCl_bF_{2-b}CH_3 \qquad (I)$$

with a an integer of 0 to 3, b an integer of 0 to 2, the sum of a and b being at least equal to 1, or small amounts of other organic products.

Fundamentally, the thermodynamic state of a fluid is defined by four interdependent variables: the pressure (P), the temperature (T), the composition of the liquid phase (X) and the composition of the gas phase (Y). A true azeotrope is a specific system with two or more constituents for which, at a given temperature and a given pressure, the composition of the liquid phase X is exactly equal to the composition of the gas phase Y. A pseudoazeotrope is a system with two or more constituents for which, at a given temperature and a given pressure, X is substantially equal to Y. In practice, this means that the constituents of such azeotropic and pseudoazeotropic systems cannot easily be separated by distillation.

For the, purposes of the present invention, the expression "pseudoazeotropic mixture" means a mixture of two constituents whose boiling point (at a given pressure) differs from the boiling point of the true azeotrope by a maximum of 0.5° C. Mixtures whose boiling point differs from the boiling point of the true azeotrope by a maximum of 0.2° C. are preferred. Mixtures whose boiling point differs from the boiling point of the true azeotrope by a maximum of 0.1° C. are particularly preferred.

At a pressure of 3 bar, the composition of the hydrogen fluoride/1,1,1,3,3-pentafluorobutane azeotropic mixture is about 60/40% by weight, i.e. a hydrogen fluoride/1,1,1,3,3-pentafluorobutane molar ratio of about 11 mol/mol.

A DETAILED DESCRIPTION OF THE INVENTION

Figure 1:
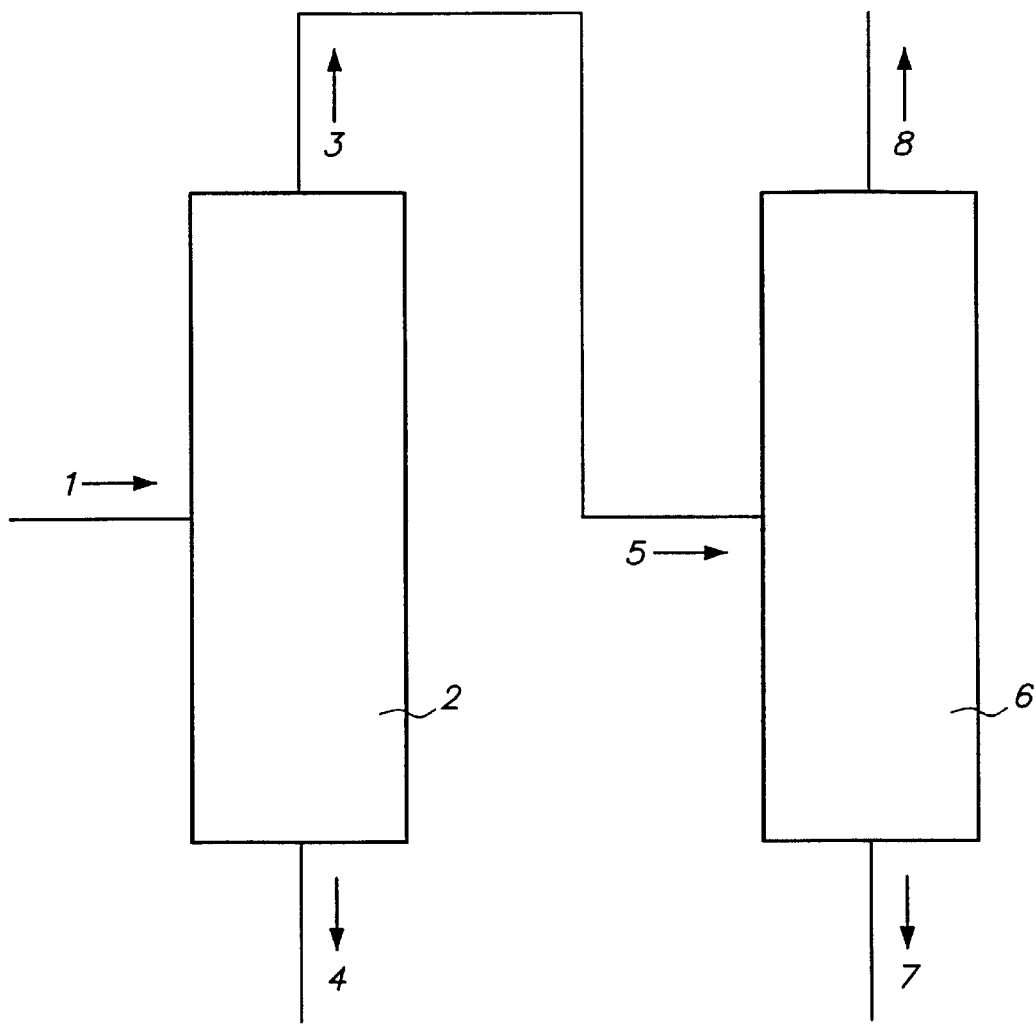
FIG. 1 represents an installation diagram which can be used to implement the process of separation according to the invention.

In the first variant of the process according to the invention, the first distillation is carried out at a higher pressure and the second distillation is carried out at a lower pressure. The numbers refer to FIG. 1. In this variant, the mixture is introduced via route (1) into a first distillation column (2) at higher pressure. At the head (3) of this column (2) an azeotropic composition of 1,1,1,3,3-pentafluorobutane and hydrogen fluoride is obtained whose composition is determined by the pressure in the column (2). At the foot (4) of this column (2), a fraction is obtained which contains 1,1,1,3,3-pentafluorobutane or hydrogen fluoride, according to whether one or other of these compounds is in excess in the mixture which is introduced via route (1) relative to the composition of the azeotrope which is decanted at the top (3), and organic compounds with a higher boiling point than the azeotrope which are optionally present in the mixture to be separated, such as chloro(fluoro) butanes of general formula (I). The composition harvested at the top (3) of the column (2) is introduced via route (5) into the second distillation column (6) at lower pressure. At the foot (7) of the column (6) a fraction is recovered which is enriched in 1,1,1,3,3-pentafluorobutane relative to the azeotropic composition recovered in (3). Preferably, in (7), a fraction consisting essentially of 1,1,1,3,3-pentafluorobutane is recovered. At the top (8) of the second column (6), an azeotropic composition is obtained which is rich in hydrogen fluoride relative to the azeotropic composition recovered in (3).

In the second variant of the process according to the invention, the first distillation is carried out at a lower pressure and the second distillation is carried out at a higher pressure. In this variant, at the foot (7) of the second column (6), a fraction is recovered which is enriched in hydrogen fluoride. Preferably, a fraction consisting essentially of hydrogen fluoride is recovered. At the top (8) of the second column (6), an azeotropic composition rich in 1,1,1,3,3-pentafluorobutane is obtained.

The invention also relates in particular to a process for the synthesis of 1,1,1,3,3-pentafluorobutane comprising at least the following steps (a) to (d):
(a) chloro(fluoro)butanes of general formula (I) are subjected to at least one hydrofluorination reaction;
(b) the reaction product comprising at least 1,1,1,3,3-pentafluorobutane and hydrogen fluoride is subjected to a separation procedure, generally a distillation, to separate the hydrogen chloride from a mixture which comprises at least 1,1,1,3,3-pentafluorobutane and hydrogen fluoride and optionally other constituents of the reaction product;
(c) the said mixture is subjected to the process of separation according to the invention;
(d) at least one fraction recovered in step (c), comprising hydrogen fluoride and optionally other constituents of the reaction product, is introduced into a hydrofluorination step.

In a preferred embodiment of the process of synthesis according to the invention, in step (c) is used the variant of the process of separation discussed above, in which the first distillation is carried out at a higher pressure and the second distillation is carried out at a lower pressure. In this case, the flow recovered at the foot of the first distillation column, consisting generally of hydrogen fluoride which is in excess relative to the azeotropic composition decanted at the top of the first distillation column and chloro(fluoro)butanes of general formula (I), as well as the flow recovered at the top of the second distillation column consisting essentially of an azeotropic composition according to the invention which is rich in hydrogen fluoride, are advantageously sent back to step (a).

Often, the mixture which is separated in step (b) and subjected to the process of separation in step (c) contains chloro(fluoro)butanes of general formula (I) as other constituents of the reaction product.

The hydrofluorination reaction of step (a) may be catalytic or non-catalytic.

Preferably, the process of synthesis according to the invention uses a chloro precursor of 1,1,1,3,3-pentafluorobutane. Particularly preferably, the chloro precursor is 1,1,1,3,3-pentachlorobutane.

The invention also relates to a method for separating hydrogen fluoride from a mixture comprising hydrogen fluoride and 1,1,1,3,3-pentafluorobutane, according to which the mixture is brought into contact in liquid phase with a solution of at least one alkali metal fluoride in anhydrous hydrogen fluoride,, an organic phase enriched in 1,1,1,3,3-pentafluorobutane and an inorganic phase enriched in hydrogen fluoride are decanted, the organic phase is separated from the inorganic phase and hydrogen fluoride is recovered from the inorganic phase. The method is often applied to mixtures comprising hydrogen fluoride and 1,1,1,3,3-pentafluorobutane in proportions at which they form an azeotrope or a pseudoazeotrope. The method is preferably applied to azeotropic or pseudoazeotropic compositions consisting essentially of 1,1,1,3,3-pentafluorobutane and hydrogen fluoride. In this way, the azeotropic or pseudoazeotropic compositions can be separated into constituents thereof.

Generally, the alkali metal fluorides used in this method are lithium fluoride, sodium fluoride, potassium fluoride and caesium fluoride. Preferably, potassium fluoride, caesium fluoride or a mixture of these two alkali metal fluorides is used.

Generally, the content of alkali metals in solution in the anhydrous hydrogen fluoride is 20 to 80% by weight. Preferably, the content is 20 to 70% by weight.

The pressure at which the mixture is brought into contact with the solution is generally 1 bar to 30 bar. Preferably, the pressure is 1 bar to 10 bar. The temperature at which the mixture is brought into contact with the solution is generally −30° C. to +50° C. Preferably, the temperature is 0° C. to 40° C.

The hydrogen fluoride may be recovered from the inorganic phase by known techniques. A distillation procedure is well suited. The recovered hydrogen fluoride may be recycled in a hydrofluorination reaction as described above.

The organic phase may be subjected to subsequent purification procedures such as, for example, a distillation to recover 1,1,1,3,3-pentafluorobutane and possibly chloro(fluoro)butanes of general formula (I) therefrom. The process of separation according to the invention is well suited as a purification procedure.

What is claimed is:

1. A process for the separation of at least one constituent from a mixture icompiring subjecting a mixture of 1,1,1,3,3-pentafluorobutane and hydrogen fluoride to at least two distillations, a first distillation being carried out at a first pressure said first distillation having a bottom product and an overhead-product and said bottom product of said first distillation contains hydrogen fluoride or 1,1,1,3,3-pentafluorobutane and said overhead product contains hydrogen fluoride and 1,1,1,3,3-pentafluorobutane in proportions at which they form at azeotrope or pseudo-azeotrope, which azeotrope has at a pressure of 3 bar a content of about 60% by weight of hydrogen fluoride and about 40% by weight of 1,1,1,3,3-pentafluorobutane which overhead product is fed in to a second distillation column and said second distillation is carried out at a second pressure which is different from the first, and at least one fraction enriched in 1,1,1,3,3-pentafluorobutane and at least one fraction enriched in hydrogen fluoride are recovered from the second distillation.

2. The process according to claim 1, in which the first distillation is carried out at a higher pressure than said second distillation.

3. The process according to claim 2, according to which a fraction consisting essentially of 1,1,1,3,3-pentafluorobutane is recovered at the bottoms of the second distillation.

4. The process according to claim 2, in which the lower pressure is 0.5 bar to 3 bar and the higher pressure is 6 bar to 11 bar.

5. The process according to of claim 2, in which the temperature at which the distillation at lower pressure is carried out is 0° C. to 60° C. and the temperature at which the distillation at higher pressure is carried out is 70° C. to 150° C.

6. The process according to claim 1, in which the first distillation is carried out at a lower pressure than the second distillation.

7. The process according to claim 6, according to which a fraction consisting essentially of hydrogen fluoride is recovered at the bottom of the second distillation.

8. The process according to claim 6, in which the lower pressure is 0.5 bar to 3 bar and the higher pressure is 6 bar to 11 bar.

9. The process according to claim 6, in which the temperature at which the distillation at lower pressure is carried out is 0° C. to 60° C. and the temperature at which the distillation at higher pressure is carried out is 70° C. to 150° C.

10. The process according to claim 1, wherein in the first distillation said overhead product is an azeotropic composition of 1,1,1,3,3-pentafluorobutane and hydrogen fluoride.

11. A process for the synthesis and recovery of 1,1,1,3,3-pentafluorobutane comprising at least the following steps (a) to (c):

(a) subjecting chloro(fluoro)butanes of general formula (I)

CClaF3-aCH2CClbF2-bCH3    (I)

where a is an integer from 0 to 3, b is an integer from 0 to 2 and the sum of a and b is at least 1, to at least one hydrofluorination reaction whereby a reaction product comprising at least 1,1,1,3,3-pentafluorobutane, hydrogen fluoride, hydrogen chloride and optionally other constituents is formed;

(b) subjecting the reaction product to a separation procedure to separate the hydrogen chloride formed from the reaction from a mixture which comprises at least 1,1,1,3,3-pentafluorobutane and hydrogen fluoride;

(c) subjecting said mixture to a process of separation of at least one constituent from a mixture comprising 1,1,1,3,3-pentafluorobutane and hydrogen fluoride, according to which the mixture is subjected to at least two distillations, first distillation being carried out at a first pressure said first distillation having a bottom product and an overhead product and said bottom product of said first distillation contains hydrogen fluoride or 1,1,1,3,3-pentafluorobutane an said overhead product contains hydrogen fluoride and 1,1,1,3,3-pentafluorobutane in proportions at which they form an azeotrope or pseudo-azeotrope, which azeotrope has at a pressure of 3 bar a content of about 60% by weight of hydrogen fluoride and about 40% by weight of 1,1,1,3,3-pentafluorobutane which overhead product is fed into a second distillation column and said second distillation is carried out at a second pressure which is different from the first, and a least one fraction enriched in 1,1,1,3,3-pentafluorobutane and at least one fraction enriched in hydrogen fluoride are recovered from the second distillation.

12. The process according to claim 11, wherein in the first distillation said overhead product is an azeotropic composition of 1,1,1,3,3-pentafluorobutane and hydrogen fluoride.

13. A process for the separation of at least one constituent from a mixture comprising 1,1,1,3,3-pentafluorobutane and hydrogen fluoride, comprising subjecting said mixture to at least two distillations, a first distillation being carried out at a first pressure said first distillation having a bottom product and an overhead product and said bottom product of said first distillation contains hydrogen fluoride or 1,1,1,3,3-pentafluorobutane and said overhead product contains hydrogen fluoride and 1,1,1,3,3-pentafluorobutane in proportions at which they form an azeotrope or pseudo-azeotrope, which azeotrope has, at a pressure of 3 bar, a content of about 60% by weight of hydrogen fluoride and about 40% by weight of 1,1,1,3,3-pentafluorobutane, which overhead product is fed into a second distillation column and said second distillation is carried out at a second pressure which is higher than the first, and at least one fraction enriched in 1,1,1,3,3-pentafluorobutane is recovered from the bottom of said second distillation and a least one fraction enriched in hydrogen fluoride is recovered from the top of the second distillation.

14. The process according to claim 13, in which the lower pressure is 0.5 bar to 3 bar and the higher pressure is 6 bar to 11 bar.

15. The process according to of claim 14, in which the temperature at which the distillation at lower pressure is carried out is 0° C. to 60° C. and the temperature at which the distillation at higher pressure is carried out is 70° C. to 150° C.

16. The process according to claim 13, in which the temperature at which the distillation at lower pressure is carried out is 0° C. to 60° C. and the temperature at which the distillation at higher pressure is carried out is 70° C. to 150° C.

17. A process for the separation of at least one constituent from a mixture comprising 1,1,1,3,3-pentafluorobutane and hydrogen fluoride, comprising subjecting said mixture to at least two distillations, a first distillation being carried out at a first pressure said first distillation having a bottom product and an overhead product and said bottom product of said first distillation contains hydrogen fluoride or 1,1,1,3,3-pentafluorobutane and said overhead product contains hydrogen fluoride and 1,1,1,3,3-pentafluorobutane in proportions at which they form an azeotrope or pseudo-azeotrope, which azeotrope has, at a pressure of 3 bar, a content of about 60% by weight of hydrogen fluoride and about 40% by weight of 1,1,1,3,3-pentafluorobutane, which overhead product is fed into a second distillation column and said second distillation is carried out at a second pressure which is lower than the first, and at least one fraction enriched in hydrogen fluoride is recovered from the bottom of said second distillation and at least one fraction enriched in 1,1,1,3,3-pentafluorobutane is recovered from the top of the second distillation.

18. The process according to claim 17, in which the lower pressure is 0.5 bar to 3 bar and the higher pressure is 6 bar to 11 bar and the temperature at which the distillation at lower pressure is carried out is 0° C. to 60° C. and the temperature at which the distillation at higher pressure is carried out is 70° C. to 150° C.

* * * * *

UNITED STATES PATENT AND TRADEMARK OFFICE
CERTIFICATE OF CORRECTION

PATENT NO. : 6,540,882 B1 Page 1 of 1
DATED : April 1, 2003
INVENTOR(S) : Ferdinand Rief et al.

It is certified that error appears in the above-identified patent and that said Letters Patent is hereby corrected as shown below:

Column 5,
Line 7, delete "iconiprising" and insert -- comprising --.
Line 15, delete "at azeotrope" and insert -- an azeotrope --.

Column 6,
Line 9, after "distillations," insert -- a --.

Signed and Sealed this

First Day of July, 2003

JAMES E. ROGAN
*Director of the United States Patent and Trademark Office*